United States Patent [19]

Tiffany et al.

[11] Patent Number: 5,508,200
[45] Date of Patent: Apr. 16, 1996

[54] METHOD AND APPARATUS FOR CONDUCTING MULTIPLE CHEMICAL ASSAYS

[76] Inventors: Thomas Tiffany, E. 1305 56th, Spokane, Wash. 99223; Bruce Weyrauch, N. 13707 Coman Rd., Newman Lake, Wash. 99025; Phillip Thayer, N. 8617 Seven Mile Rd., Nine Mile Falls, Wash. 99026

[21] Appl. No.: 963,457

[22] Filed: Oct. 19, 1992

[51] Int. Cl.$^6$ ................................................ G01N 35/00
[52] U.S. Cl. .................. 436/44; 436/46; 436/530; 436/165; 436/166; 436/1.69; 422/66; 422/67; 435/7.91; 435/287.1; 435/288.3; 435/288.4; 435/288.7
[58] Field of Search .................. 422/56, 66, 67, 422/63–65; 436/169, 165, 166, 43, 530, 44, 46; 435/4, 291, 7.92

[56] References Cited

U.S. PATENT DOCUMENTS

| | | | |
|---|---|---|---|
| Re. 28,339 | 2/1975 | Maxon | 254/50.4 |
| 3,036,893 | 5/1962 | Natelson | 436/170 |
| 3,261,668 | 7/1966 | Natelson | 422/56 |
| 3,368,872 | 2/1968 | Natelson | 422/66 |
| 3,554,700 | 1/1971 | Maxon | 436/44 |
| 3,607,079 | 9/1971 | Maxon et al. | 436/44 |
| 4,013,418 | 3/1977 | Plakas | 422/52 |
| 4,071,315 | 1/1978 | Chateau | 436/518 |
| 4,178,153 | 12/1979 | Sodickson | 436/165 |
| 4,327,073 | 4/1982 | Huang | 436/44 |
| 4,552,723 | 11/1985 | Adams et al. | 422/66 |
| 4,568,520 | 2/1986 | Ackermann et al. | 422/66 |
| 4,752,448 | 6/1988 | Wells et al. | 422/56 |
| 4,767,702 | 8/1988 | Cohenford | 422/56 |
| 4,803,154 | 2/1989 | Vo et al. | 422/56 |
| 5,049,487 | 9/1991 | Phillips et al. | 422/56 |
| 5,075,077 | 12/1991 | Durley, III et al. | 422/56 |
| 5,169,600 | 12/1992 | Ishizaka et al. | 422/66 |

FOREIGN PATENT DOCUMENTS

| | | | |
|---|---|---|---|
| 959392 | 12/1974 | Canada. | |
| 971772 | 7/1975 | Canada. | |
| 191640 | 8/1986 | European Pat. Off. | 436/169 |
| 2316111 | 3/1973 | Germany. | |
| 2027664 | 2/1987 | Japan | 436/169 |
| 2102159 | 5/1987 | Japan | 436/169 |

Primary Examiner—Robert J. Warden
Assistant Examiner—N. Bhat
Attorney, Agent, or Firm—Wells, St. John, Roberts, Gregory & Matkin

[57] ABSTRACT

A system for high performance automated chemical analysis includes a video camera photometer with a computer-controlled interference filter wheel. A fluidics system delivers ultramicro sample and reagent volumes in the 0.05 to 5.0 microliter range to a supporting analytical media. The media is precisely positioned relative to the photometer by an x-y axis reaction media holder capable of accurate and precise positioning of the ultramicro reaction spots. The reaction media can consist of absorbent cellulose sample/reaction strips or microscopic sized multiple wells. A data and reduction system monitors multiple simultaneous reactions within a common test area of the analytical media to provide final quantitative reports. The method for conducting multiple chemical assays involves placing small volumes of sample/reagent combinations at discrete locations about a common test area on the analytical media and simultaneously measuring resulting optical changes at each discrete location.

25 Claims, 10 Drawing Sheets

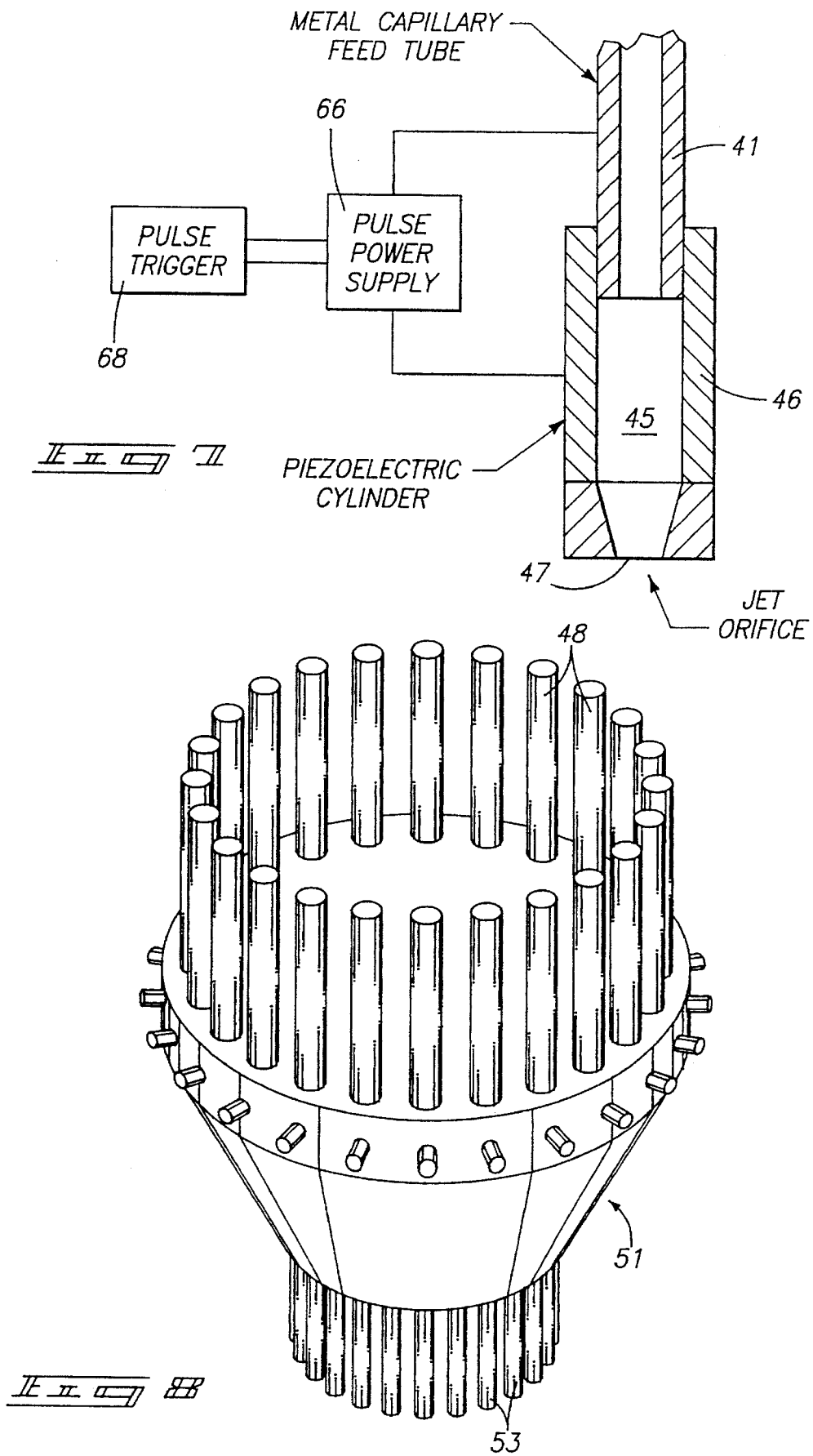

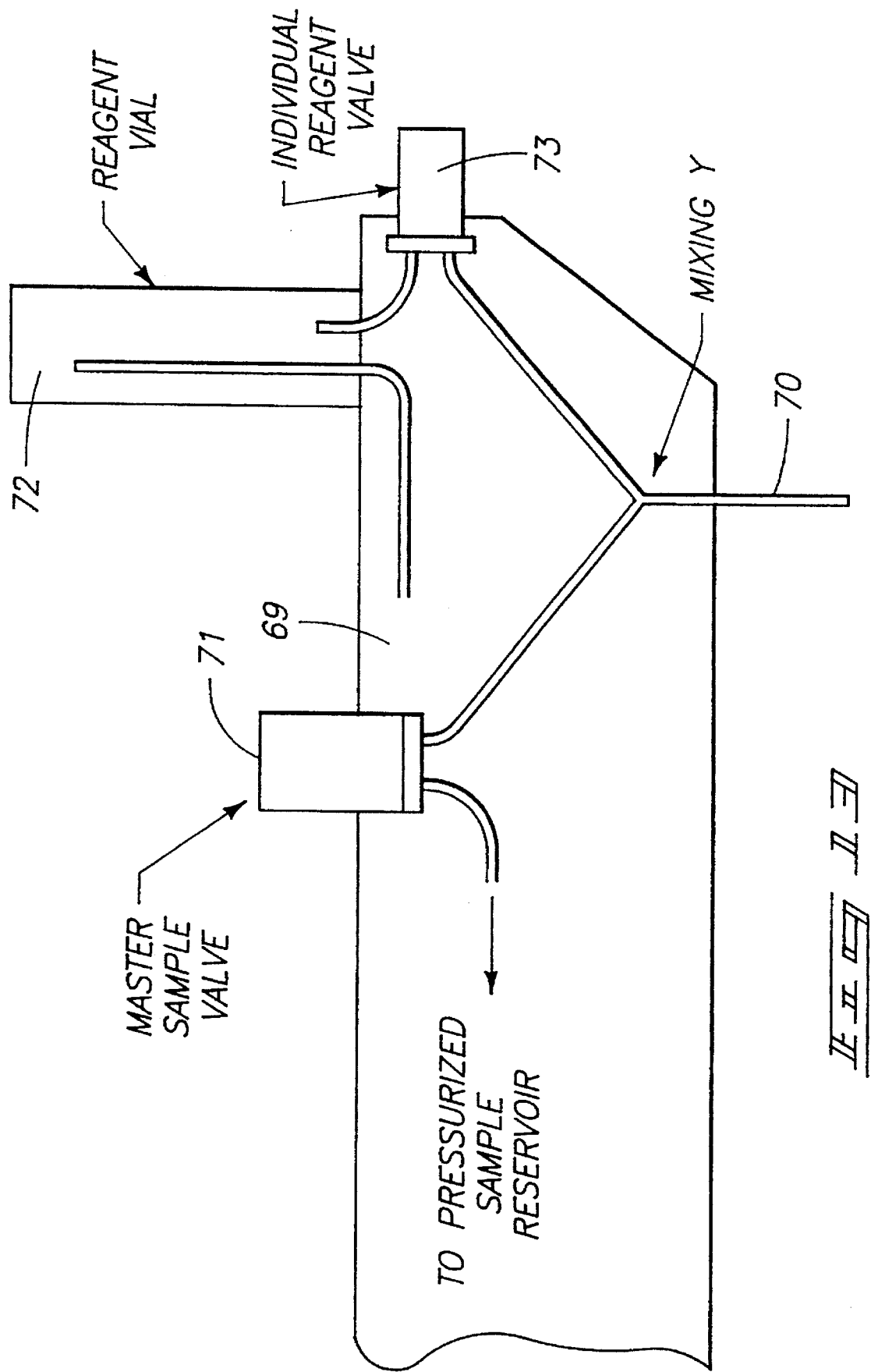

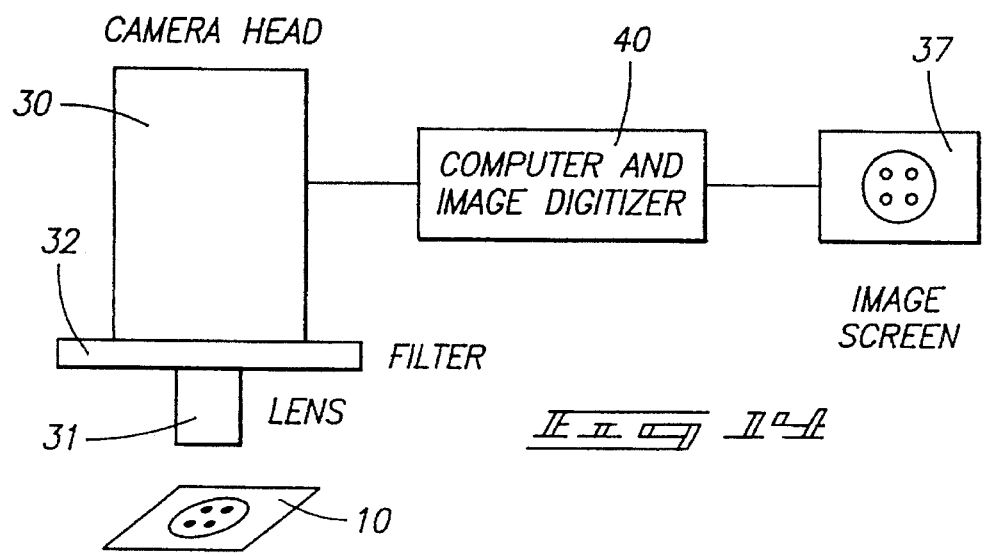
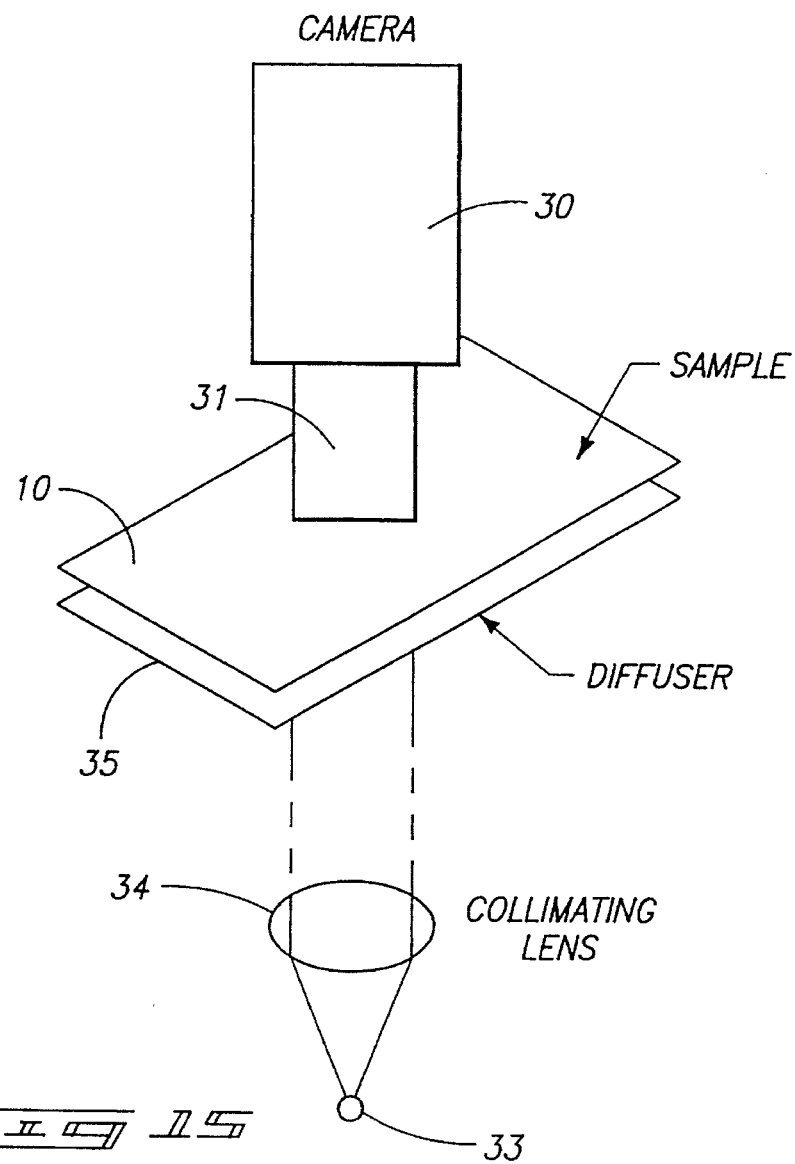

METHOD AND APPARATUS FOR CONDUCTING MULTIPLE CHEMICAL ASSAYS

TECHNICAL FIELD

This disclosure pertains to high volume chemical analyzers of the type utilized in analytical chemistry, particularly for clinical chemistry and in vitro diagnostic applications. An example of such an application is clinical blood and serum testing using a plurality of reagents.

BACKGROUND OF THE INVENTION

Automated chemical analytical systems for biomedical and clinical applications have seen many changes over the past 25 to 30 years. Early equipment of this type could perform basic electrolyte, glucose and bun (urea) measurements at a rate of 60 samples per hour. Improved equipment introduced in the early 1970's allowed for analysis of up to 19 chemistries per sample at a rate of about 90 samples per hour. These systems introduced quality control monitoring and other software features that provided high quality laboratory results.

Centrifugal analyzers later introduced the concept of automated multiple chemistries that could take place in the same time/temperature environment. These later systems featured the ability to perform relatively high speed kinetic analysis on up to forty separate samples per analytical run. Centrifugal analyzers advanced the concept of single, stable reagents for several common clinical substrates and enzymes.

Originally configured as a batch analyzer, the centrifugal concept has evolved to a random access tool for analysis purposes and has been coupled to ion-specific electrodes to form the basis of a modern moderate throughput chemistry analyzer. Applications for this type of analyzer have expanded to include enzyme kinetics, enzyme immunoassays, specific protein assays, coagulation assays, and agglutination blood grouping assays. Optics capabilities have been added and expanded in these systems to include spectrophotometric, chemiluminescence, fluorescence, turbidimetric and nephelometric measurements. Sample and reagent volumes have been decreased from the more traditional 500 microliter ranges to a range of 100 to 200 microliters.

The late 1970's and early 1980's demanded a change in philosophy of automated chemical analyzers and systems designed for biomedical research. Technology and reliability are now assumed to be a given and high performance is required in such systems. The important driving forces for instrument development have become non-supervised automation, multiple analytical functions within a single analytical system, discrete operation where one to more than 20 chemistries are performed per sample, simplicity in analytical operations, internal quality checks, bidirectional interfaces to host computers, high throughput, and cost effective operation. Typical automated chemical analyzers in the moderate range (for small to medium laboratories) must now have random access operation, discrete test capabilities and the capacity for producing 1000 tests per hour. High throughput analyzers must be capable of producing from 5000 to 10,000 test results per hour.

Automated analyzers are currently facing the need to meet new technological challenges (i.e., growing numbers of immunoassays on different media and DNA/RNA probes) while also performing present methodology (i.e., substrates, enzymes, electrolytes, immunoassays for therapeutic drugs, drugs of abuse, and thyroid function) and while further experiencing regulatory and budgetary pressures requiring higher accuracy and improved cost effectiveness. Tightened regulation of the operation of such systems requires more stringent proficiency testing, which will increase the need for quality control checks, improved accuracy, and precise performance. In addition, the number of qualified medical technologists has decreased, greatly increasing the need for automated multi-function analytical systems designed to be operated by personnel of limited skills.

All current high volume chemistry analyzers are very complex, require extensive electrical and distilled water service, and occupy substantial laboratory space. They are competitive because they are fast, use small amounts of reagent, are relatively easy to use, and are operated on a random access basis. They can be adapted to provide more than 35 chemistries on-board, including immunoassays.

New automated analyzer systems now must have increased technological capabilities, but must also cost less to purchase and, as important, must cost less to operate. Finally, such systems must exhibit a unique economy of reagent consumption to be acceptable in this field.

The present system arose as a direct result of an attempt to simplify the technology used in the currently-expanding dried blood spot market that is being explored in great detail by the life insurance testing industry. This led to testing of a system that can perform multiple chemistries or immunoassays on a single spot of whole blood or serum in the same time and temperature dimension. By simultaneously performing multiple analyses, the throughput of the system can be very competitive with the most complex of the current chemistry analyzers.

The system described below evidences several distinct advantages: (1) it can be relatively small and less complex than current systems, (2) it does not require extensive plumbing and washing systems, (3) it can be part of a whole blood system using a dedicated special sampling device, (4) it can use relatively simple liquid reagents, (5) its sample and testing media permit employment of complex immunoassay systems, including DNA and RNA probes, and (6) it lends itself to positive sample identification schemes from bedside to final result.

BRIEF DESCRIPTION OF THE DRAWINGS

Preferred embodiments of the invention are described below with reference to the accompanying drawings, which are briefly described below.

FIG. 7 is an enlarged cross sectional view illustrating a piezoelectric dispensing jet;

FIG. 8 is a perspective view of a reagent-dispensing manifold;

FIG. 13 is a diagrammatic sectional view of a premix manifold for sample and reagent materials;

FIG. 14 is a diagrammatic view of the detector system;

FIG. 15 is a diagrammatic view illustrating detection by transmission; and

DETAILED DESCRIPTION OF THE PREFERRED EMBODIMENTS

Figure 1:
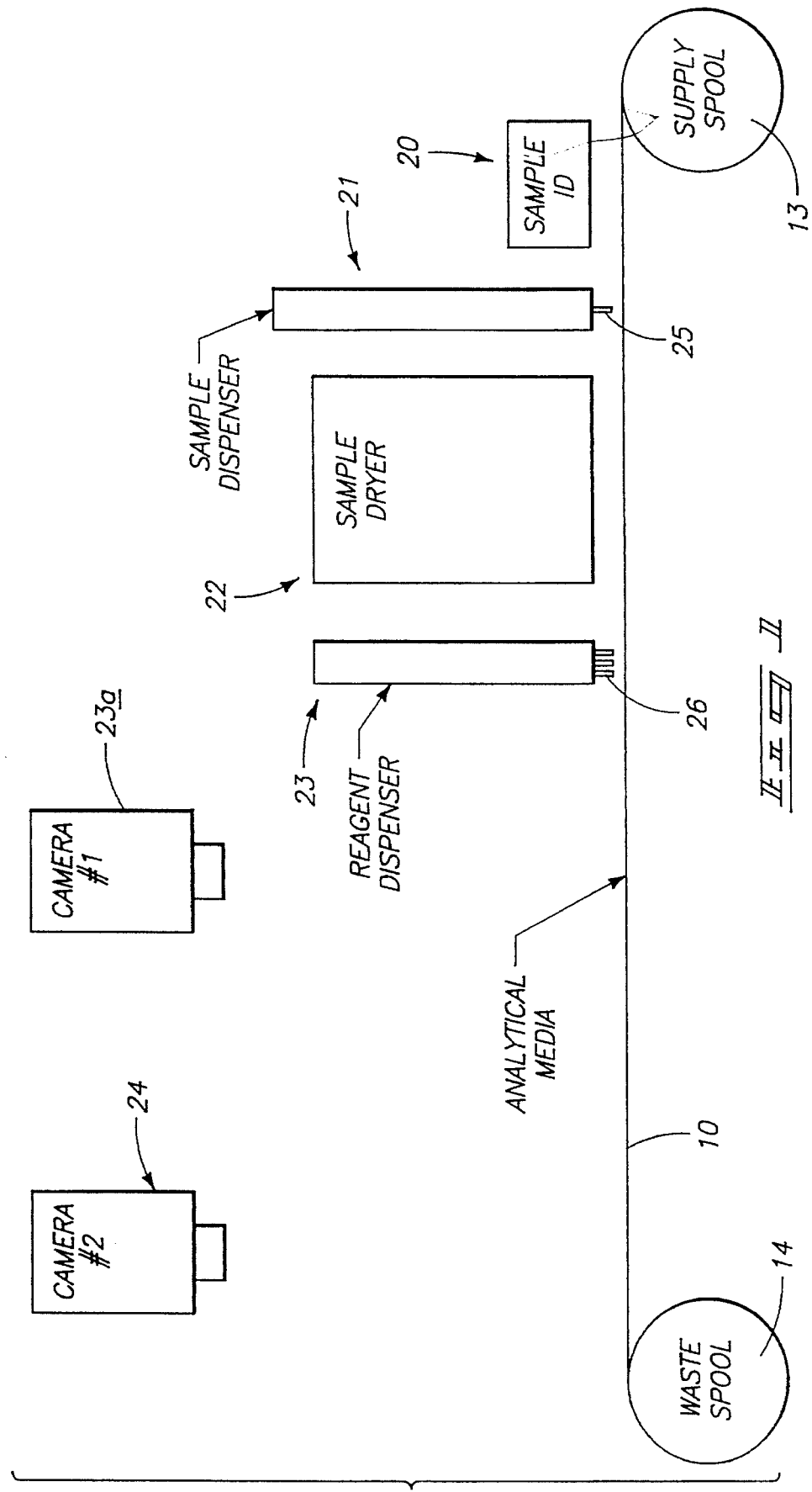
FIG. 1 is a diagrammatic elevational view of the system.

This disclosure of the invention is submitted in furtherance of the constitutional purposes of the U.S. Patent Laws "to promote the progress of science and useful arts" (Article 1, Section 8).

The proposed analytical system is directed to the conduct of multiple chemical analyses on a liquid sample, such as blood or serum, but not exclusive to these body fluids. The method utilized in this system involves placing small volumes of sample/reagent combinations at discrete locations spaced from one another about a common test area on a supporting analytical carrier. Optical changes that occur at each discrete location on the supporting analytical carrier are measured simultaneously to thereby provide a quantitative analysis with respect to the resulting sample/reagent reactions.

The basic building blocks of the system are:

1. A supporting analytical carrier. Sample and reagent(s) are combined and supported at small discrete locations about a common test area of the carrier for analysis purposes.

2. A mechanism for dispensing multiple reagents or test samples about the common test area on the media. Dispensing can be accomplished simultaneously about the common area or serially. Mixing can take place prior to dispensing or on the carrier.

3. A detector system for simultaneously monitoring individual reactions at the discrete locations about the common test area of the analytical carrier. Video technology is utilized to capture information concerning multiple reactions for downstream binary processing to yield quantitative test results.

The primary application of this system pertains to high volume chemistry testing. It can be embodied within a robotic and automated system wherein various types of samples are placed on a supporting analytical carrier. The carrier may be either an absorbent matrix or a microcuvette plate.

The detector system is capable of performing a variety of chemical and immunochemical tests in a repetitive and controlled manner. An optics measuring system can perform different types of luminescence measurements including transmission, reflectance, fluorescence, chemiluminescence, time resolved fluorescence, fluorescence polarization and light scattering. Both single and multiple reagent tests can be conducted by use of this system. Applications pertaining to blood and serum testing include routine chemistries and immunoassays of varied types of samples. The system can be physically embodied within a high throughput bench top analyzer. It also can be incorporated into a small dedicated analyzer having applications in special chemistries, food chemistry, hospital or environmental testing, as well as in other industrial applications.

SYSTEM OVERVIEW

The preferred embodiment described below uses a video camera to simultaneously measure optical changes in a multiplicity of chemical reactions; each occupying a discrete region of space.

The discussion starts with a description of two instruments: one using an absorbing material to support the reaction and the other using microcuvettes. The discussion continues with descriptions of the various subsystems. In general these subsystems can be applied to either instrument.

ABSORBENT MATRIX BASED SYSTEM

FIG. 1 shows a first embodiment of an instrument designed according to this disclosure. The system consists of six stations: a sample identification station 20, a sample dispensing station 21, a sample drying station 22, a reagent dispensing station 23, an initial monitoring station or camera 23a and a final monitoring station or camera 24. Some of these stations may be combined as the technology advances.

Figure 2:
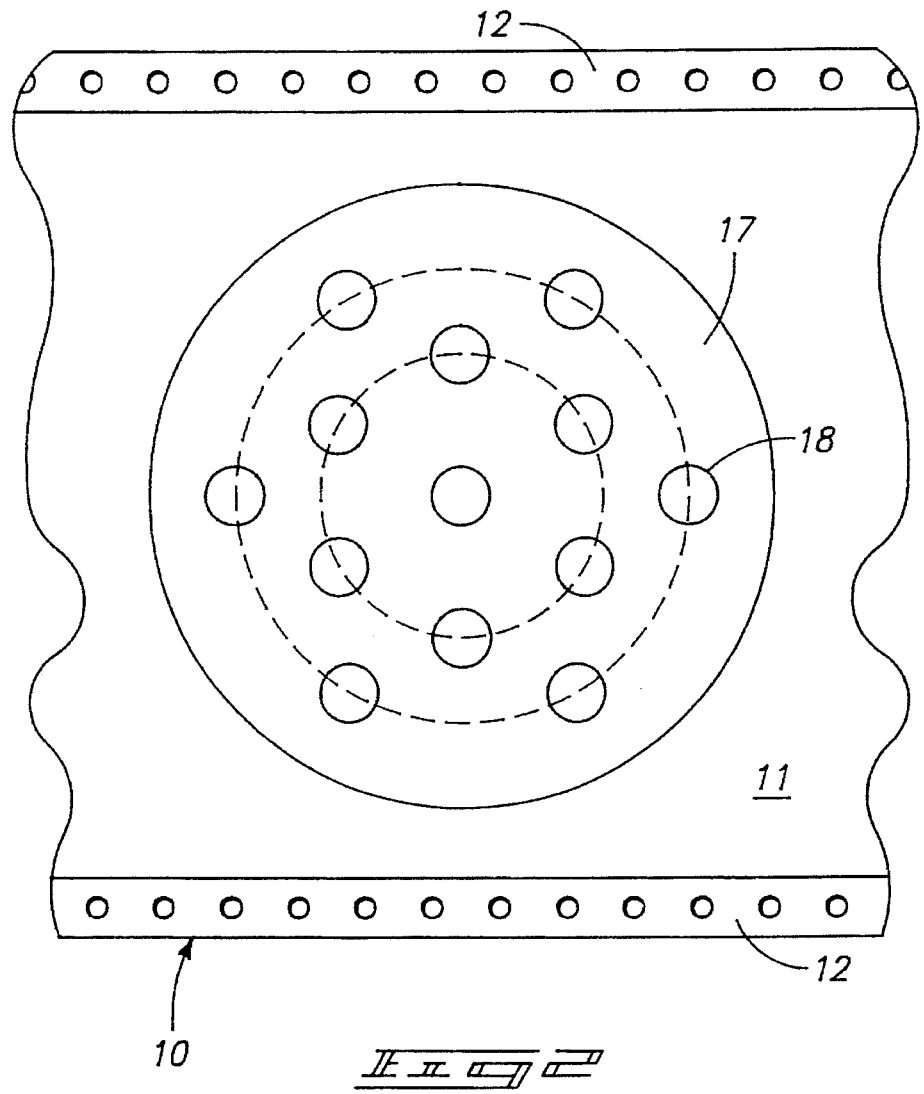
FIG. 2 is a plan view of test media employed in the present system.
Figure 3:
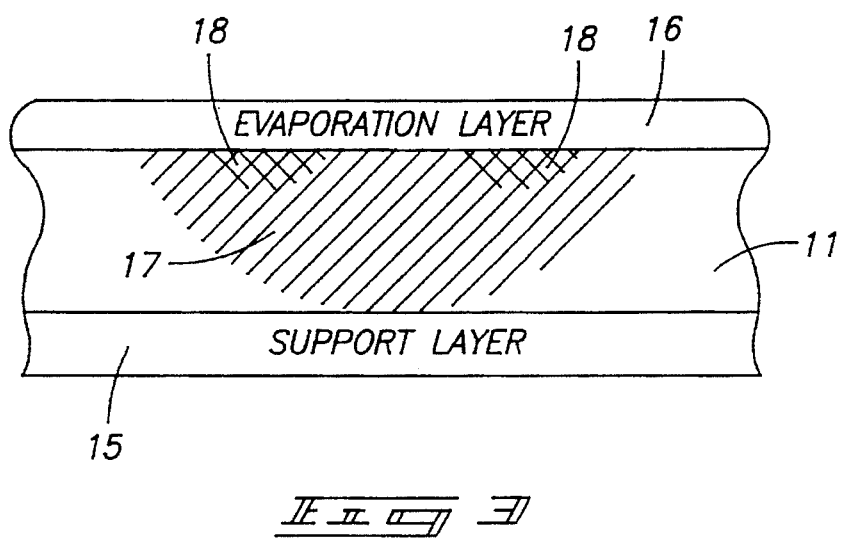
FIG. 3 is an enlarged diagrammatic view taken across the media shown in FIG. 2.

This embodiment uses an absorbent matrix 10 as the analytical carrier or media, illustrated in FIGS. 2 and 3. Matrix 10 is a continuous strip of absorbent fibrous sheet material 11, such as paper. Matrix 10 has borders 12 which include one or more rows of apertures for tractor feeding the strip between a supply spool 13 and a waste spool 14 (FIG. 1). The supply spools should be sized for at least 8 hours of continuous operation at 450 samples per hour.

A liquid sample is directed onto the upper surface of matrix 10 by sample dispensing station 21. Location of a resulting sample spot 17 is assured by accurate positioning of the dispensing mechanism relative to the matrix 10 and by uniformly diffusing the sample within layer 11.

To ensure stoichiometry, all moisture is removed from the sample by drying station 22 prior to the dispensing of reagents at station 23. This assures comparable reaction results about the entire sample area 17 regardless of the depth of penetration within layer 11 by a particular reagent.

An initial absorbance reading for each reagent is taken by monitoring station 23a immediately following the dispensing of sample and reagent. A final reading is made by final monitoring station 24. To assure calibration between the two monitoring stations, measurements are also made with respect to a non-reactive reference area on the analytical matrix.

A variation of this embodiment uses a circular disk of an absorbent matrix instead of the continuous strip. A disk can accommodate multiple sample spots. The matrix is moved through the stations as described above, except that all photometric measurements can be made at a single station. Analyses requiring measurement at variable time intervals and multipoint rate analyses are more easily accommodated because of the ease of returning to the camera station. Maximum system throughput can be realized if the disks are spotted with sample and dried off-line so that the function of the instrument is restricted to spotting with the selected reagents and making of optical measurements. Alternatively, the disks can be preprocessed with lyophilized reagent and only sample added by the instrument.

Absorbent Matrix

As shown in FIG. 3, absorbent layer 11 is laminated to a structural support layer 15 of sheet material impervious to liquids and capable of providing consistent dimensional qualities to the laminated matrix. A transparent evaporation layer 16 overlies the exposed upper surface of sheet 11 to provide evaporation control during the measurement cycle. Additional layers may be used for separation of sample components or for concentrating and drying of the sample.

A liquid sample of sufficient volume to saturate the absorbent layer 11 of analytical matrix 10 is directed onto the upper surface of matrix 10 by sample dispensing station 21. The sample of blood, serum or other liquid forms a spot at the upper surface of layer 11 whose diameter is of the order of 1 to 17 mm. Location of the resulting sample spot is assured by the accurate position of the dispensing mechanism relative to matrix 10 and by the uniformity of diffusion of sample within the layer 11.

The spot pattern shown in FIG. 2 includes a relatively large circular sample area 17 defining the common test area about the matrix and a plurality of discrete small reagent areas 18 which are spaced from one another within the test area.

Depending upon the number of small areas 18 desired in each monitoring sequence, the larger area 17 is contained within a region of 1 to 50 mm in diameter. The smaller areas may be of the order of 0.5 mm to 10 mm in diameter. They are each designed to contain 0.1 to 0.5 microliters.

Common test area 17 is identified at the sample identification station 20. As an example, information pertaining to the identification of a sample being tested is encoded as a bar code or other machine-readable code applied to the upper surface of matrix 10. Alternately the sample matrix is pre-coded and the identifying number is entered by a camera. This information, which can be monitored by any conventional reading equipment (not shown), is used to identify samples and/or reagents as they pass through the various operative stations of the equipment.

MICROCUVETTE BASED SYSTEM

Figure 4:
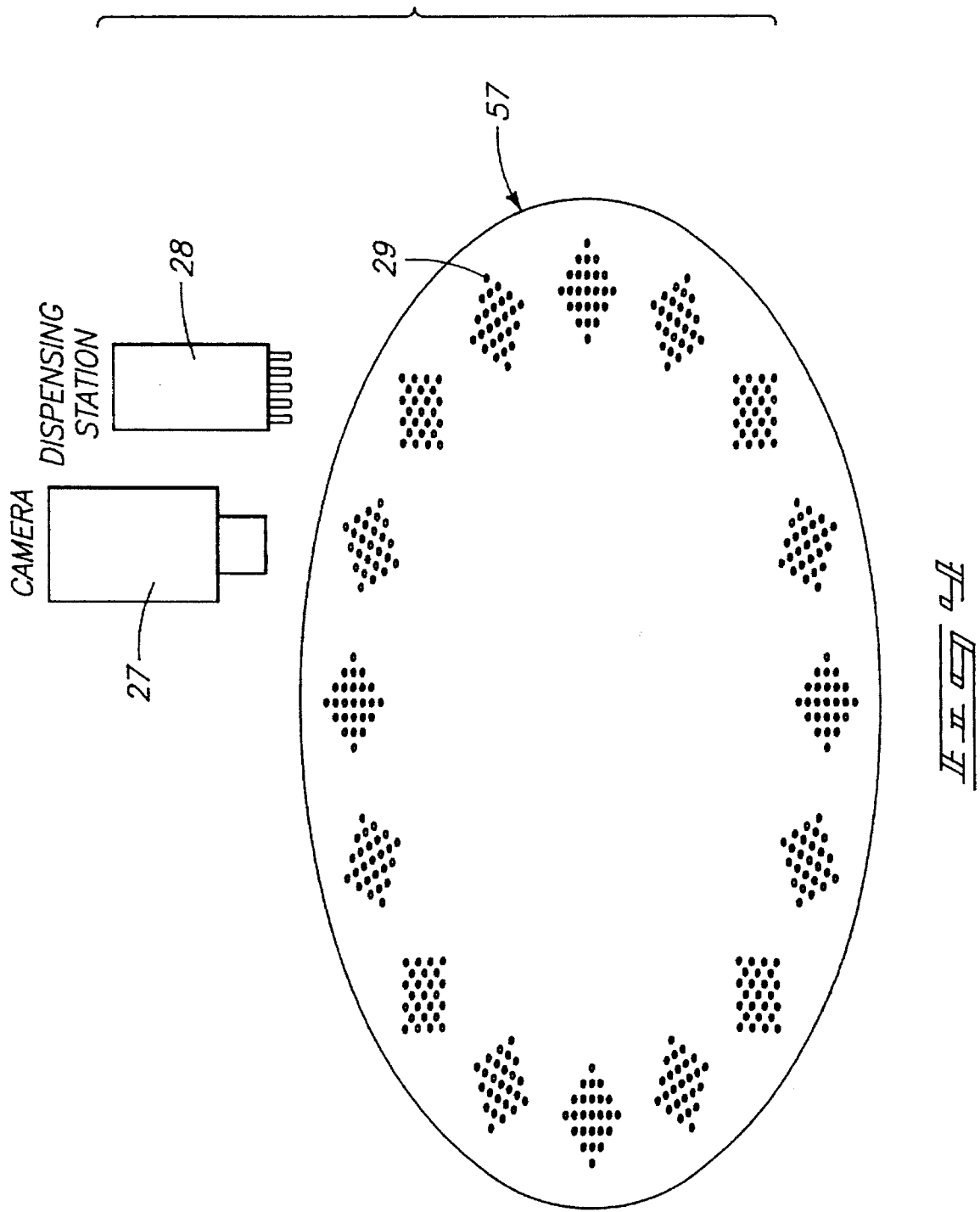
FIG. 4 is a perspective view of microcuvette-based test system in accordance with the invention.
Figure 5:
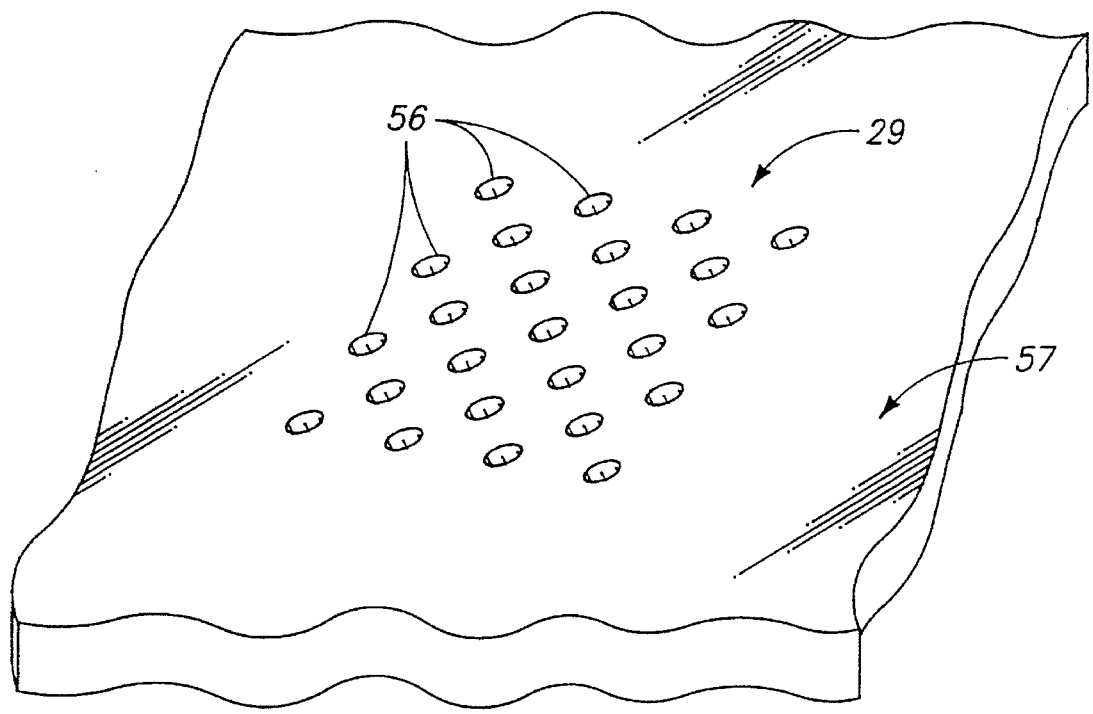
FIG. 5 is an enlarged perspective view illustrating the microcuvettes of FIG. 4.

FIGS. 4 and 5 represent a second embodiment of an instrument designed according to this disclosure. The system includes two stations: sample/reagent dispensing station 28 and an analysis station shown by camera 27.

The analytical carrier is a circular plate 57 of material transparent to visible and ultraviolet light. It should contain at least 40 or more sets, 29, of microcuvettes 56. Each set 29 contains on the order of thirty microcuvettes 56 in a pattern similar to that shown. Plate 57 is rotatable about a central vertical spindle (not shown). An indexing arrangement (not shown) is provided to monitor and control the rotational position of the plate 57 about the axis of the supporting spindle.

Sample/reagent dispensing station 28 is a ganged premix dispenser used to dispense sample and reagent into microcuvettes 56. Immediately following each dispensing step, the plate 57 rotates, bringing the next microcuvette set 29 into camera view for photometric measurement. Dispensing and measurement of the microcuvette sets are interlaced to accommodate the timing requirements of individual analyses.

Stoichiometry is assured by the volumetric accuracy and flow characteristics of dispensing station 28.

Microcuvette Plate

As shown in FIG. 5, the microcuvette plate 57 consists of a transparent plate, e.g. glass, styrene or acrylic with a number of small depressions. The depressions that form the microcuvettes can be either cylindrical or truncated conical in shape.

In the configuration shown, sample and reagent flow into microcuvettes 56 located just below the optical surface of plate 57. Each micro cuvette is simply an open recess or well formed through the top surface of the liquid impervious plate 57. The multiple reactions that subsequently occur in the microcuvettes 56 are monitored from an overhead camera.

Because of the small reaction volume, an evaporation barrier such as a film of silicone oil is applied to the upper surface of liquid in each microcuvette 56 to control evaporation. The oil is preferably mixed with the dispensed sample and reagent. The transparent oil has a mass density less than water. Since it is not miscible it floats to the upper surface to control evaporation.

The common test area, exemplified by the area 29 of the circular plate, is identified by its position relative to the indexing mechanism. The correspondence between common test area and sample identification is maintained by a computer that controls motion of the circular plate.

THE DISPENSING STATION

The dispensing technologies used in this system fall into two classifications: post-mix and pre-mix. Each is applicable to both an absorbent matrix or microcuvette plates.

Post Mixing

In the preferred embodiment shown in FIG. 1, sample and reagent are dispensed independently. Larger area 17 is formed from one or more drops of sample (or reagent) and smaller areas shown at 18 are created by one or multiple micro drops of reagent (or sample).

Post mixing of the test components relies on the liquid dispersion through the porous matrix to achieve the desired sample/reagent ratio. The matrix is first impregnated with either sample or reagent by saturating the matrix with a dilute solution. The matrix is then completely dried, thereby retaining sample (or reagent) within the porous structure of the matrix. The second component, either reagent or sample, is applied to the matrix, again saturating it. Since the matrix is dry before applying each fluid and is sequentially saturated during application of the fluids, the retention qualities of the matrix will determine the sample/reagent ratio.

Post mixing encompasses four distinct modes, all producing patterns similar to that shown in FIG. 2. One or more of areas indicated at 18 might be untreated to serve as a reference, or might be treated with substances used for quality control purposes.

The four modes are as follows:

Mode 1. Single Large Sample with Subsequent Smaller Reagents.

Mode 2. Multiplicity of Small Reagents with Subsequent Larger Sample.

Mode 3. Single Large Reagent with Subsequent Smaller Samples.

Mode 4. Multiplicity of Small Samples with Subsequent Larger Reagent.

Modes 1 and 2 are particularly suited to random access analyzers in which requested tests are run on each sample as it is presented to the system. Mode 2 is particularly attractive because either individually controllable or ganged dispensers can be used, yet all reactions start simultaneously with the application of sample. Further, mode 2 lends itself to prepackaged reagent rolls, which eliminates on-board reagent handling.

Prepackaged reagent rolls are strips of matrix materials having discrete areas of selected reagents impregnated along their length. They provide a convenient way of changing to a different battery of reagents and provide a safe and convenient way of disposing of sample and reagent. Each roll can be encoded so that the analyzer can detect the mix of reagents available along the matrix.

While drying is used to concentrate or fix the sample in a solid phase matrix, other ways to achieve this include use of separation layers or agents included in the matrix to bind and dry the sample.

In the embodiment shown in FIG. 4, sample and reagent liquids are dispensed independently into the microcuvettes. Mixing is accomplished by the application of some form of agitation such as ultrasonic or mechanical vibration of the microcuvette plate. The second component, reagent or sample is dispensed simultaneously into all cuvettes so that reactions will start simultaneously.

Unit Dispensers

Syringe

Figure 6:
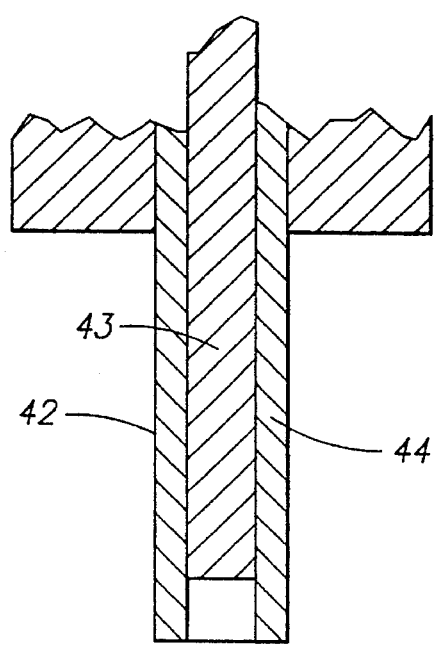
FIG. 6 is an enlarged cross sectional view of a plunger micro dispenser.

FIG. 6 shows a digital, ultramicro dispenser 42, consisting of a fine sapphire plunger 43 that can be stepper driven within a small diameter hollow tube 44. In concept, the dispenser 42 works like a syringe. Liquid is drawn into the hollow capillary tube 44 by retracting plunger 43 and is expelled by extending it. Normally, the volumes of reagent required by this system are sufficiently small that the expelled liquid forms a drop on the end of capillary tube 44. The exposed drop can be transferred onto matrix 10 by bringing tube 44 into contact with the top surface of the matrix sheet.

Chem-Jet

Chem-jet utilizes the technologies of ink jet printing to dispense measured amounts of reagent or sample. The jet may be a piezoelectric device or a pressurized channel controlled by a fast acting micro valve.

FIG. 7 illustrates a piezoelectric chem-jet. Reagent is drawn into a jet cavity 45 through a connecting feed tube 41 by capillary action and is dispensed by producing an outward going shock wave on a piezoelectric cylinder 46. The shock wave, produced by a pulse power supply 66 and operated by a trigger circuit 68 imparts sufficient velocity to the fluid in an orifice 47 to overcome surface tension and break away from the fluid bulk. Dispensing jets of this type can be made very small and can be easily assembled in an array to simultaneously dispense a plurality of reagents or samples.

The accuracy of the dispensed volume need not be great when using a porous analytical carrier since the porous matrix controls relative concentrations as it is saturated.

In the case of either technology, the reagent may be associated with its own dispensing device or all reagents may use a common dispensing device. In the former case the concept of an inexpensive disposable chem-jet cartridge much like ink jet cartridges is very attractive. In the case of either technology, the dispenser is controlled independently so that only requested analyses are run on each sample. The number of reagents in the repertoire exceeds the space available on the sample spot; thus, a selected subset of analyses can be run, provided the number does not exceed the capacity of the sample spot.

The sample spot capacity is of the order of 30 tests. To accomplish this, at least some of the dispensers must have the capability of being aimed so that unused areas on the sample spot may be utilized by less frequently used analyses. In the latter case of a common dispenser, a multiplicity of fluidic channels and valves is required to route reagents and wash water. Further, the dispenser must either be aimed or positioned to produce the desired reagent pattern.

Ganged Dispensers

When multiple reagents are to be dispensed it is desirable to spot them simultaneously.

A ganged dispenser is an array of micro dispensers held together in a dispensing head. Ganged dispensers have two variations: independently operated dispenser units and commonly operated dispensing units. In either case the individual dispensing units form a dispensing head in which the relative position of individual dispensers is fixed.

Independently Operated Ganged Dispensers

Figure 9:
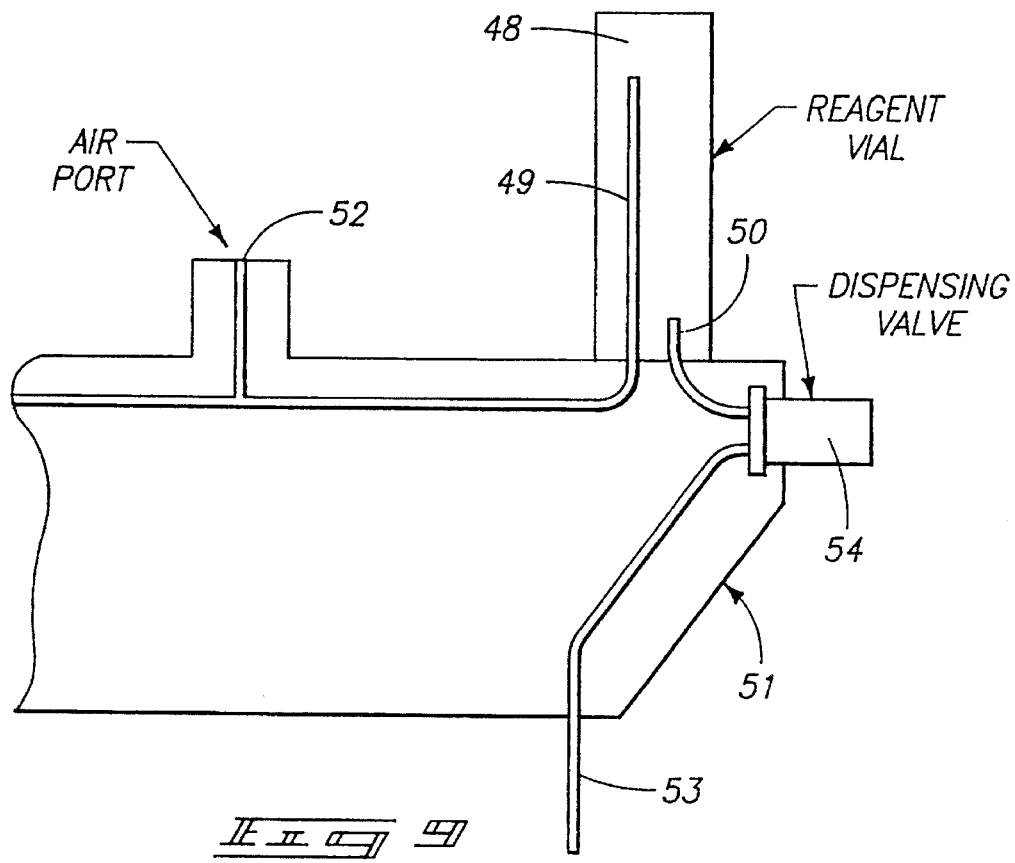
FIG. 9 is a diagrammatic sectional view taken across the manifold shown in FIG. 8.

FIGS. 8 and 9 show a dispensing manifold which integrates multiple reagent reservoirs and a dispensing mechanism. Inverted reagent containers 48 have a pressure tube 49 and a reagent outlet tube 50 inserted into them. Within manifold 51 all pressure lines are brought together at a pressurized air port 52, while the outlet tubes 50 are brought down to dispensing probes 53 within a small area at the bottom of the manifold 51. Between dispensing operations the reagent is prevented from flowing by closing off each outlet tube 50 with a micro valve 54. A slight pressure is maintained within reagent containers 48 so that a momentary opening of the reagent valves 54 causes reagent to be dispensed.

Another technology consists of a plurality of chem-jets held together in a dispensing head. Each jet operates in the fashion described earlier under unit dispensers. As the matrix 10 passes under the dispensing head only the desired reagents are projected onto the matrix.

Common Operation of Ganged Dispensers

As one example, a spotting head is comprised of multiple hollow probes 26 (FIG. 1) mounted in a supporting block which moves from a reagent table (not shown) to a position above the analytical carrier. Probes 26 must be individually capable of retaining sufficient reagent to saturate a 1.5 mm spot.

Figure 10:
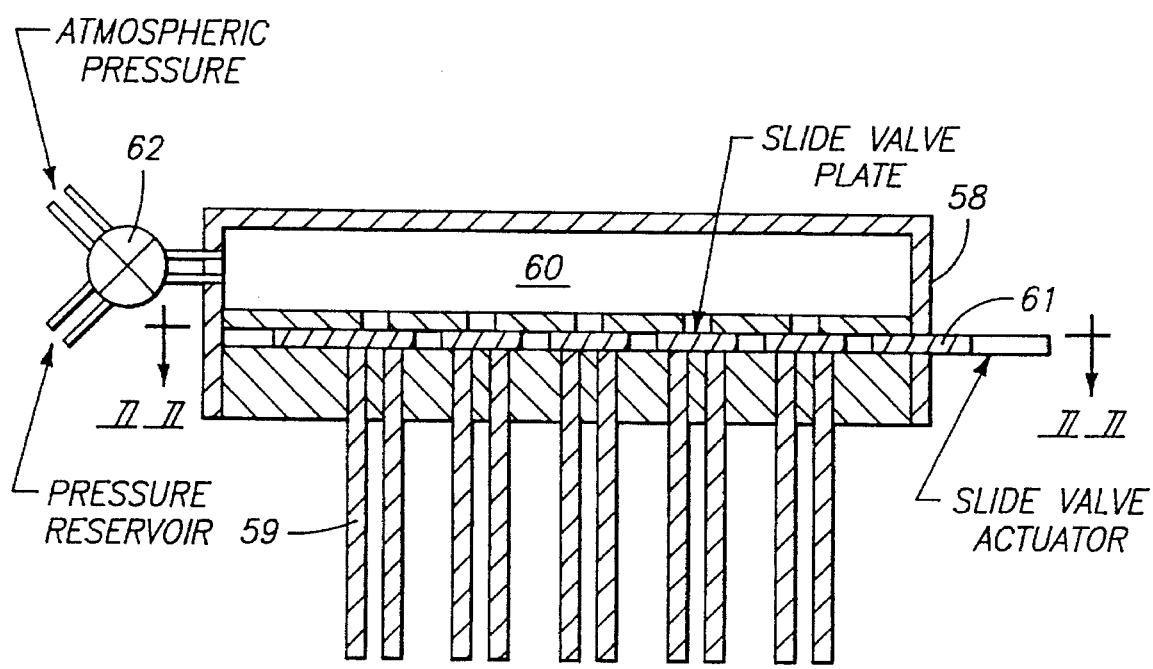
FIG. 10 is a sectional view of a ganged dispenser.
Figure 11:
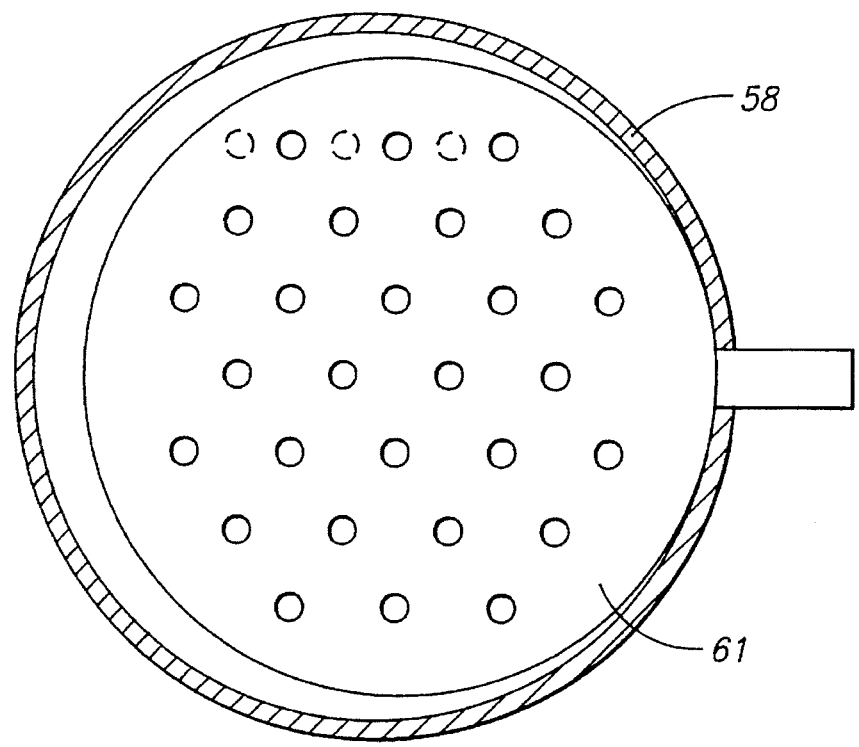
FIG. 11 is a sectional view taken along line 11—11 in FIG. 10.

FIGS. 10 and 11 show the structure of a multiple transfer head. A block 58 contains an array of capillary tubes 59 which terminate at the lower surface of an interior head cavity 60. An apertured slide valve plate 61, containing one hole for each capillary tube 59, is movably mounted across the bottom of cavity 60. Plate 61 is free to move from side to side, thereby opening or sealing the upper ends of tubes 59. Tubes 59 are filled by placing their outer ends into a supply of one or more reagents (not shown). During standby, the head rests on the reagent supply block with transfer tubes 59 in contact with reagent and with the slide valve closed, thereby restricting reagent evaporation at the interior of cavity 60. To initiate a dispensing operation, the head is lifted with reagent trapped within the tubes 59. When the head is moved to the analytical carrier, the head cavity is pressurized slightly by operation of a control valve 62 and the slide valve is opened, thereby simultaneously expelling the reagents from the individual tubes 59.

PRE MIXING

The premix mode relies on the fluidic characteristics of the channels leading into the mixing volume to establish the sample/reagent ratio. The mixing ratio is a consequence of the dimensions of the flow channels, the viscosity of the fluids and the pressure applied to each channel. Mixing may occur within the fluidic manifold with subsequent dispensing or may occur outside of the manifold, most likely at the surface of the analytical carrier.

Unit Internal Pre-mix Dispenser

Figure 12:
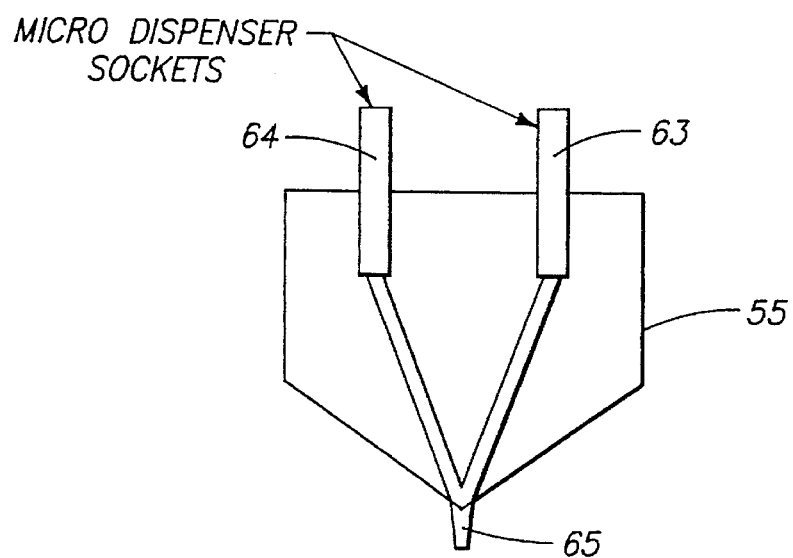
FIG. 12 is a sectional view of a flow injection block.

FIG. 12 illustrates a discrete mixing block 55 in which two micro dispensers 63 and 64, for sample and reagent respectively, are positioned at the upper end. Activating the dispenser plungers causes reagent and sample to mix prior to being dispensed through a common capillary probe 65. Individual spots of sample and reagent are positioned on the slide 57 or matrix 10 by either moving the receiving surface or the dispenser, using a high speed x-y positioner.

Ganged Internal Pre-mix Dispenser

FIG. 13 illustrates a mixing manifold 69 patterned after the dispensing manifold of FIGS. 8 and 9. Excess sample is dispensed into a sample reservoir (not shown) which is subsequently sealed and pressurized. Sample and reagents are mixed by simultaneously operating master sample valve 71 with appropriate reagent valves 73. After each dispensing procedure, the sample fluidic channels are flushed with water and the sample reservoir is refilled with the next sample.

External Pre-mix Dispensers

The chem-jet technology is particularly well suited for this application. Sample and reagent chem-jets are aimed at the same spot within the micro well and are activated simultaneously so that mixing occurs as the two streams collide.

THE DETECTOR STATION

The use of low noise CCD (Charge Coupled Device) technology is well established for applications such as military surveillance, space exploration, astronomy and scientific research. This disclosure extends the application of such technology to commercial multichannel analytical instrumentation, particularly in the biomedical field.

Unlike traditional photometer systems, the present system reads multiple reactions simultaneously. Each camera, such as camera 30 shown in FIG. 14, has an associated filter wheel 32, containing narrow band interference filters. Filter wheel 32 is located along the optical path in such a manner that minimum band broadening occurs. The motion of filter wheel 32 is synchronized with camera 30 such that each filter covers the camera field of view during image acquisition. The size of the common test area and focal length of the lens are selected so that reactive areas 18 (FIGS. 2 and 3) contain no fewer than 20 array elements in each image captured by the camera 30.

Output from each camera 30 is digitized and stored in CPU memory using dual ported DMA (Direct Memory Access) circuitry. The dual ported memory allows access to the images by analysis software while new images are being stored.

A 12-bit ADC (Analog to Digital Converter) having a S/N (Signal to Noise) ratio in excess of 70 db should be used in digitizing the signal. Because of the relatively long readout time of 3 seconds, the speed of the ADC can be of the order of 10 microseconds per conversion. The requirement of a 12-bit ADC is not to extend measurement to large optical densities but to provide precision for analyses in which there is small change in light intensity.

The resulting images can be viewed on a monitor screen 37. The color levels and light intensities of the images can be graphically analyzed to determine the state of each reaction at two points in time, thereby providing an accurate indication of the tested content for the sample. In each case, in preparation for an analysis, the reference areas of the sample are measured and iris or exposure time adjustment is made to produce a signal approaching the saturation limit of the CCD/ADC.

CCD (Charge Coupled Device) technology is proposed for image capture because of its superior S/N ratio performance over other current arrays. The sensitivity of CCD arrays in the near ultraviolet range can be dramatically increased by etching away the array substrate material and illuminating the array from the backside. To achieve the desired camera noise levels, the CCD array needs to be cooled to at least −30° C. This temperature can be achieved using air cooled Peltier devices.

Exposure is controlled by an automatically adjustable iris and by adjusting integration time. Changing intensity of incandescent light sources is unsatisfactory because of accompanying shifts in spectral distribution. If xenon flash lamps are used, coarse exposure control can be achieved by use of multiple flashes.

The use of long integration times for exposure control introduces significant dark signal noise. The effects of dark signal build up can be reduced by using dark signal biasing; however, random differences between the actual dark signal and the bias represent a noise signal which can not be eliminated.

ILLUMINATION

The common test area is illuminated for the purposes of acquiring photometric data from the reaction spots. This can be accomplished by use of incandescent lamps, xenon arc lamps, halogen tungsten lamps or high intensity strobed xenon flash lamps. Two alternative lighting arrangements are illustrated in FIGS. 15 and 16.

In FIG. 15 the common test area on matrix 10 is backlit, thereby providing the traditional absorbance of a spectrophotometer. Light from a point source 33 is directed through a collimating lens 34 and diffuser 35 to the analytical matrix 10.

Figure 16:
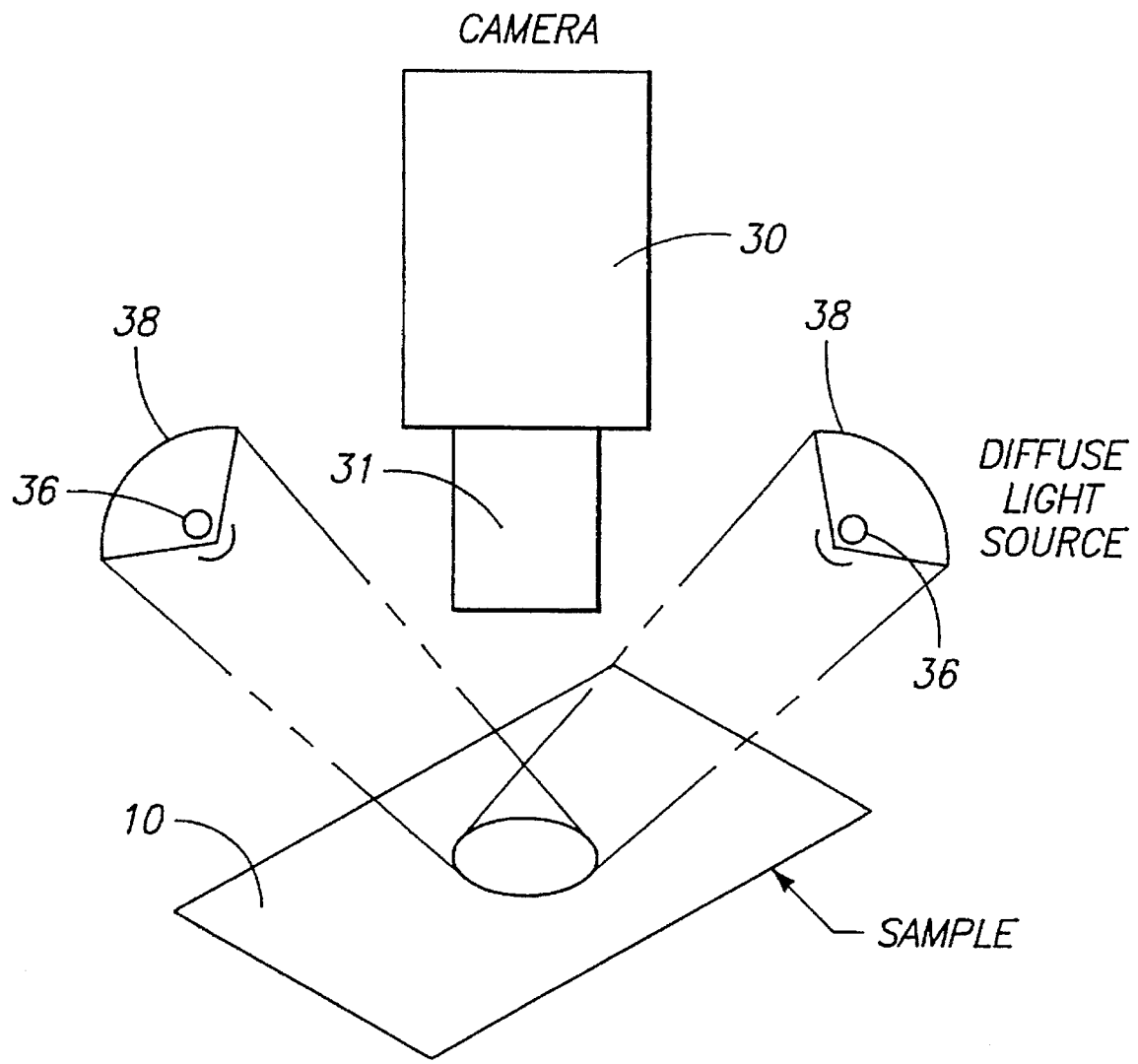
FIG. 16 is a diagrammatic view illustrating detection by reflectance.

In FIG. 16 the common test area is illuminated from above, as in a reflectance spectrophotometer. A pair of diffuse light sources 36 illuminate analytical matrix 10.

Illumination of the common test area should be uniform. Small variations can be corrected through use of blanking, provided the relative illumination between blank area and other areas of interest about the common test area are constant in time or at least vary slowly in relation to data acquisition times. Accordingly, the sample area is to be protected from external light sources. The sample area is best illuminated by a diffuse light source located so specularly reflected light does not strike the detector.

DRYING STATION

If drying is used to bind the sample in the matrix, it must be accomplished rapidly without adversely affecting the sample. Hot air, microwave technology or infrared lamps might be used within sample drying station 22 (FIG. 1). Drying station 22 might also enclose sample dispensing station 21 so as to maximize the drying time along the moving length of the analytical matrix 10.

DATA ACQUISITION AND ANALYSIS

Absorbance Photometry

Light penetrating a distance x into an absorbing material decreases in intensity according to Lambert's Law:

$$I = A \exp(-bx)$$

where A is initial intensity and b is the absorption coefficient. In general, the absorption coefficient b is a linear function of the analyte concentration so that the concentration is given by:

$$C = -q(\log(I/A)) = q\,OD$$

where q is a constant involving the pathlength of the cuvette and the molecular absorption coefficient. The optical density OD is the negative logarithm, base 10, of the fraction of light penetrating a depth x.

Reflectance Photometry

The optical processes that take place within an absorbent or fibrous analytical matrix 10, as illustrated in FIGS. 2 and 3, are complex. Light entering the fibrous matrix 10 undergoes multiple scattering from the fibers. In scattering from fiber to fiber, light is absorbed in a manner characteristic of the intervening sample/reagent solution. Some light will continue to penetrate the fibrous matrix and, if the matrix is thick enough, will be completely absorbed. The rest of the light will reemerge from the upper surface of the analytical matrix 10, producing the characteristic color of the reaction.

In general, absorption by the fiber also occurs, thus absorption at the characteristic wavelength is the result of competing processes. Further, the relationship between scattering and absorption by the fiber depends upon the relative index of refraction between fiber and surrounding media. Consequently the relationship between sample concentration and light intensity is not as simple as in the case of absorbance photometry.

A discussion of this relationship can be found in the articles: "Reflectance Digital Matrix Photometry", by Neely (Clin. Chem. 29/4 1038–1040 (1983)) and "Multilayer Film Elements for Clinical Analysis: General Concepts" by Curme (Clin. Chem. 24/8 1335–1342 (1978)), which are hereby incorporated into this disclosure by reference. These articles refer to the linearization transform of Williams-Clapper described in "Multiple Internal Reflections in Photographic Color Prints", by Williams (Journal of the Optical Society of America 44/7 595–599 (1953)), which is hereby incorporated into this disclosure by reference. The form of the Williams-Clapper transformation is:

$$OD = a + b(RD) + c/(1 + d \exp(gRD))$$

where a, b, c, d, and g are adjustable constants, RD is the measured reflectance density and OD is the equivalent optical density of the analyte. The constants a, b, c, d, and g are to be determined through calibration of each analyte/matrix combination.

Corrections

Prior to applying the above equation, corrections must be made to the intensity measurements.

Dark Field Correction

The output of the CCD camera is not absolutely zero in the absence of light. Thus the dark field output of each pixel must be subtracted from subsequent intensity measurements.

Blank Correction

In practice, concentrations are determined by making measurements on intensity changes over a period of time. During the time of such measurements, external influences such as variation in source intensity or variation in amplifier gain may invalidate the readings. Blanking is a method for isolating these variations. Simultaneous readings are made on the sample and a non-reactive blank. The relative intensity is then determined as the ratio of the sample intensity to blank, both of which have been dark field corrected.

Thus relative intensities, given by:

$$I = [I(\text{sample}) - I(\text{dark})]/[I(\text{blank}) - I(\text{dark})]$$

are used in the calculation of optical density. The relative intensity is essentially independent of camera and lighting. Thus, measurements on the sample may be made with different cameras at independent stations.

Calibration

Calibration is generally used to eliminate effects resulting from uncertainty of pathlength, variations in temperature and/or non-defined kinetics of the reaction. When the kinetics are first order, a single high calibrator is used to establish the calibration line. When the kinetics are non-first order, a series of calibrators are used so that interpolation techniques may be used to determine concentration.

Calibration must be done in such a way that the physical characteristics of the reagent/sample combination and the analytical matrix 10 are identical for both the calibrator and the sample. To eliminate systematic error, it is desirable to process samples and calibrators in parallel.

ANALYSIS PROCEDURE

Prior to analysis, the common test area within the field of view of the camera 30 representing reactive areas of the sample must be identified. This has been done to date by viewing the sample on a video screen and manually creating areas of interest. In an automated system, the locations of these areas will be precisely defined by the position of the dispenser head. Accordingly, sample media handling will be done in such fashion that reactive areas will be brought into congruence with predefined areas within the video image.

As with photomultiplier systems, intensity data is read by the detector system. Sampling algorithms extract the multiple values of 12-bit intensity data associated with the reaction and combine them into a single value representative of the sample.

Prior to dispensing samples to the area 17 a dark field measurement is made by covering the camera lens and storing the dark field pixel by pixel.

One of the areas 18 is selected as a blank area to which only water or other blanking material is applied during dispensing of sample. This area will be used in determining the relative intensity of all other sample areas.

Samples are dispensed to the other sample areas contained within the area 17.

Immediately following sample dispensing, a baseline image of area 17 is stored.

The difference between the baseline and the dark field is stored as the dark field corrected baseline by subtracting one image from the other, pixel by pixel.

The relative intensity is computed by dividing the dark field corrected baseline by the mean intensity of the blank area.

In like fashion, a second relative intensity image is obtained at a later time or different wavelength.

The second image is divided by the first thereby producing the reaction image showing the effects of the reaction.

The mean intensity of pixels within each area 18 is computed. The mean intensity of the blank area should be very nearly 1.

The negative logarithm of each area 18 is computed. This represents the change in optical density. If an absorbent matrix is being used these values need to be linearized by using the Williams-Clapper transformation or by using a series of calibrators.

Finally, the concentration is determined from the change in optical density, OD.

CHEMISTRIES

With respect to blood and serum testing, the above-described system is applicable to all routine chemistries and appropriate immunoassays. Chemistries of interest include: glucose, urea, uric acid, creatinine, cholesterol, triglycerides, calcium, albumin, total protein, LD, AP, AST, ALT, CK, GGT, bilirubin, sodium, potassium, chloride, $TCO_2$, and inorganic phosphorous. Applicable immunoassays of interest: Thyroxine (T4), T3 uptake, TSH, dilantin, phenytoin, theophylline, and digoxin. Other chemistries and immunoassays can be applied to this system.

Commercially available reagents can be selected within the absorbance range of interest (e.g. 340 to 700 nm). These can all be monitored at selected wavelengths by the CCD camera system.

Solid Phase Chemistry

In an article appearing in *American Biotechnology Laboratory News*, April 1989, Kremer and Tabb presented a discussion about the Schleicher & Schuell cellulose paper, its properties, and the characteristics of the reaction surface most favoring sensitive sharply defined reaction zones. The SS cellulose paper is made primarily from cotton fibers and contain 85% to 90% alpha cellulose. When the cellulose slurries are made into the final filter material, they are poured onto a moving wire mesh. Felt material is placed on top of the slurry for forming purposes. With the slurry on the wire, water is drained away through the action of table rolls, foils, and suction boxes and the sheet is formed. Thus two sides become identified on any sheet of cellulose filter paper, the smooth side facing the felt and the rougher side facing the wire mesh. The smooth side is the preferable side for optical measurements. In addition to this, during the drainage of the water from the pulp slurry through the wire, a large proportion of the fiber fines are removed from the wire side surface of the sheet. This factor has importance with regard to the application of soluble colored reagents, or indicator dyes, in that different dyes vary in their affinity for fines and long fibers, some dyeing the longer fibers preferentially and some dyeing the fines preferentially.

Most present filter test strips apparently are prepared by precipitating the reaction materials into the matrix of the cellulose fiber material. They achieve this either by immersing the filter material in slurries of reaction components suspended in nonaqueous solvents or through multiple applications of the reaction material with suitable intermediate steps to cause the reaction material to form a fine precipitate in the cellulose fibers. The current thinking is that it is the very fine particulate nature of the minimally aqueous soluble reagent, and its high dispersion through the capillary structure of the paper, which produce the particular sensitivity and acceptable reactive performance of such products as glucose test strips and urine dip stick multiple test strips. There are several features of these dry reagent strips which are summarized in the following paragraphs:

The fine particulate nature of the reagent results in an extremely large increase in its total surface area, which in turn allows a minimally soluble reagent to react with the desired components in an applied test solution with acceptable reaction velocity.

The high dispersion of reagent throughout the capillary structure with exposure of large reagent surface area results in an excess of the reagent always being available when small amounts of material are being detected.

The ability to apply successive sample applications to the same reaction site may enhance the detection of trace quantities of a desired test component in dilute solutions.

For reactions occurring with reagents precipitated into the cellulose fibers and sample applied to the reagent, the minimal solubility of the reagent which results in the slow release and diffusion of reactive material from its surface ensures that the majority of reactions which occur will take place at or near the surface of the reagent particles. It is believed that this leads to the formation of a reaction product coating of the solid reagent particle instead of the formation of a nucleating grouping of solid reaction products in solution which would result in a precipitated particulate in which the bulk of the material is buried from the viewing surface. The latter is not a problem if the media is translucent and the optical readings are absorbance rather than reflectance.

Most chemists are taught to think of reactions occurring in aqueous or non-aqueous solutions with plenty of degrees of freedom for all reactants. The thought of reactions occurring in highly ordered minimally soluble conditions is important to this disclosure. Since there is a stoichiometric relationship between analyte and reagent it seems that it will always be necessary to have reagent in excess to drive the reaction to completion. The analysis of the present testing system is not necessarily bound to the current perspective of reactions (analyte and reagent) occurring randomly in solution.

Due to the rapid immobilization of the reaction products at their site of formation, very sharply defined reaction zones are formed with no diffusion or bleeding of product from the area of formation. This is a key concept and is exploited in this system. It is important to remember that it deals in reaction quantities that are about 100 to 1000 times less than are presently used in classical wet chemistry systems. In this system, sample is always in excess, thus requiring methods to concentrate reactants.

In current systems where sample is applied to a reagent test strip, the bulk of the applied test solution is rapidly wicked away from the point of application or site of reaction and the products that are formed there. This capillary or filtering action assists in the creation of sharply defined reaction zones and the removal of potentially obscuring soluble secondary reaction products or other colored materials contained in the originally applied sample solution.

In the present system, it is preferred that the sample be placed on the media before the reagent. This requires that a uniform concentrated sample area be provided with the sample immobilized in such a way that multiple reagents can be applied in appropriate concentrations and carrying solutions as to form solid phase reaction zones on the surface of the support material or to form uniform reaction zones for reflectance analyses.

When solid phase reaction zones are achieved, reaction sites can be washed to remove colored soluble secondary reaction or sample products not related to the reaction product of interest, thereby improving visualization and the reduction of background interference.

A smooth white background of the paper media provides an ideal contrast to formed colored reaction products. Further the smooth reflective surface and translucent nature of such a media allows light to be applied either directly to (reflectance) or passed through (absorbance) the media to best achieve quantitative analysis of the monitored reaction products.

The above discussion items refer primarily to high purity reagent grade cellulose fiber paper. From these discussions the properties of the cellulose paper provide a multiplicity of benefits in the production and performance of test medias facilitating reaction support, dispensing of liquid components, sample application, test component immobilization, reaction concentration, and filtering of liquid components.

EXPERIMENTAL RESULTS

A number of tests have been performed to demonstrate the solid phase chemistry concept and to establish that the video system is capable of producing quantitative results. Some of the results have been derived from direct visual observation and others from use of a camera.

Experimental tests of the above system to this point have utilized a moderate resolution CCD camera with a manual filter holder. Several solid phase chemistry experiments have been performed to demonstrate successful addition of reagents to a sample spotted on cellulose papers as well as other solid phase media.

Reagent volumes in the range of 0.2 to 0.5 microliters have been used to produce glucose results. Four chemistries have been monitored simultaneously on the same sample spot to show initial feasibility of measuring multiple chemistries. Also performance of ultramicro wet chemistries have been successfully demonstrated to show feasibility of an ultramicro well system.

During initial experiments to look at the properties of the various reaction supports, hardware was assembled to measure reflectance from the observed reactions and software algorithms were developed to follow the reactions. The CCD camera was fitted with an interference filter holder which contained four filter positions in a linear fashion.

Experiments Using Absorbent Matrix

The first experiments conducted with this system investigated the feasibility of putting a sample spot on paper to produce an area 17 as shown in FIG. 2 and then dropping small amounts of aqueous reagent to produce superimposed smaller spot areas 18 to determine whether a visible reaction would occur. This was demonstrated on a blood sample for five chemistries: GGT, cholesterol, triglyceride, uric acid, and glucose. The test results demonstrated that reactions producing variable color intensities could be distinguished in the small submicro quantities of reagent spots.

Schleicher and Schuell product 903 Specimen Collection Paper was used for the initial feasibility experiment. 25 microliters of various controls were spotted on the 903 paper. One microliter of enzymatic trinder cholesterol reagent, prepared four times concentrated, was spotted on two levels of control and a cholesterol standard. The results were pinkish reaction spots appearing at the spot of the reagent application to the sample spot. The intensity of the pinkish color appeared to be proportional to the amount of cholesterol in the sample.

This experiment showed that visually discernable colors can be seen at physiological concentrations of a clinical significant analyte (cholesterol). Although this is only one of several analytes of interest it is an indication for success in this approach because the reaction spot was very visible at clinically important cholesterol levels. Furthermore, the spot was visible when using a very small amount of reagent. It was apparent that reagent spots could be of an even lesser amount with more than one reaction spot placed on a single sample spot.

The next set of experiments involved visual examination of three of the Schleicher and Schuell materials to include SS 903 (Cellulose blotter), SS 470 (Cellulose blotter), and SS 24 (Glass fiber filter). Sample spots of 10 microliters and 20 microliters were applied to each of the media to examine the resulting spread of sample on the materials. Cholesterol reagent was prepared four times concentrated to use as a color indicator. The spots were examined visually and by use of a CCD camera with a 500 nm narrow band pass interference filter.

The SS 470 material is a thicker blotter material than the SS 903 material. This property allows more material to be absorbed by this media than by the SS 903 media. 10 microliter spots on the 470 material showed about half as much spreading as did the 20 microliter spots. The SS 903 material, due to the fact that it is 50% thinner than the SS 470 material, showed much greater spreading of both the 10 microliter and 20 microliter samples.

The silicon glass fiber material (SS 24) showed some very interesting properties when sample was applied. 10 and 20 microliters of normal control, abnormal control, and cholesterol calibrator material were applied to the glass filter material in duplicate. About one microliter of cholesterol reagent two times concentrated was applied after the spots had dried. Spots were dry in less than 15 minutes. The glass fiber material showed less spreading than the cellulose blotter materials. The reactions appeared to occur throughout the media where the reagent was applied to the sample spot and the media was translucent where the reagent was applied and through the media where the reagent migrated through the spotted glass fiber material. The SS 24 glass fiber material has an organic binder to increase tensile strength, which could become a contamination problem with regard to other reactions.

The first algorithm developed was an absorbance program which measured the changing absorbance of the reactions about every 10 to 15 seconds. The first experiment with this equipment and program involved glucose tests using a Trinder method. 25 microliters of abnormal and normal control serum were spotted onto SS 470 filter paper. The spots were made in duplicate and allowed to dry for 15 minutes. A commercial glucose reagent was reconstituted according to manufacturer's instructions. One microliter of reagent was placed on a spot and the reactions was monitored at 500 nm by the CCD camera and photometric software.

The normal control material showed greater absorbance change (132 units) than the abnormal control (112 units) even though the normal control had a value of 92 mg/dl and the abnormal control has a value of 262 mg/dl. Repeated reactions produced similar results. These tests verified that the camera and software worked and that the results were reproducible. An unexpected result was that the reactions were not stoichiometric and actually appeared to be in substrate excess. As a result of these initial experiments several observations were made:

1. The reagent, even at one microliter, is absorbed through the SS 470 cellulose paper. The completed reaction colored spots could be seen at the front and back of the paper.

2. The currently recommended sample volume to reagent volume for the glucose reagent is 1:12.5. The sample volume to reagent volume used in these experiments was approximately 2:1 to 1:1. Therefore the substrate was approximately 25 to 50 times too concentrated for ideal reaction conditions.

3. There appeared to be some effect of wetting agent on the intensity and duration of final reaction color. When 300 mg/dl glucose control was spotted on filter paper with and without 0.1% Triton X-100, the control material with wetting agent appeared to show more intense color.

4. Drying the sample spot on the paper before applying the reagent appeared to enhance the color.

5. Stoichiometry of the reaction was maintained through two actions. First: the sample saturated the analytical media. Because of uniformity of the matrix material, the center of the spot consisted of a uniform distribution of sample. Second: all moisture was removed from the sample and was replaced by the reagent diluent. If the sample is not completely dry when reagent is applied, saturation by the reagent solution will occur at a lower concentration of reagent molecules.

6. Material flows through the paper, both reagent and control. By using this phenomenon when flowing sample into the media but subsequently preventing reagent from flowing through the paper or other media, one can concentrate the colored spot, minimize washing away of sample, and be able to utilize both sides of the paper for sample analyses. This can be accomplished by mixing reagents with appropriate wetting agents, using different viscosity diluents, using non-aqueous or aphotic mixtures of reagents, fixing the sample into a media, such as nitrocellulose, which binds protein to the matrix, or by using paper additives that immobilize the sample in the media.

An additional series of experiments examined the effect of concentration of sample on the stoichiometry of the glucose reaction. Sample was diluted ⅓ with 0.1% Triton X-100 wetting agent. Reagent was concentrated 10 times by reconstituting the reagent with less diluent. Twenty microliter spots of diluted normal, abnormal, and calibrator material were placed on the SS 470 media. Different dilutions of calibrator were prepared for reference purposes. Reagent (0.5 microliter) was subsequently placed on the various diluted control spots. The relative absorbance readings for the spots were determined at 500 nm with the CCD camera and an automated data acquisition program. The resulting calibration curve was obtained.

The use of diluted experimental sample and concentrated reagent resulted in a more stoichiometric relationship between the sample and reagent. A second set of experiments with a slightly greater sample dilution was subsequently performed. This experiment showed a reasonable linear curve up to 500 mg/dl.

From the results of these experiments it was determined that the run to run variation between similar sample spots does not appear to be large and it appears to be reasonably reproducible. It was also observed that calculation of control values by use of the calibrator graph resulted in glucose values (normal and abnormal) that were consistent, but the normal control showed a matrix effect where the control value was consistently about 20 to 25 mg/dl higher than its expected value. Increasing color intensity, immobilizing the sample with a wash of undesirable background component, and development of better algorithms for reflectance measurements should improve such results.

The feasibility of multiple measurements on one sample spot about the media was subsequently attempted by use of a program for simultaneously measuring up to four separate reactions. The tests involved placement of reagent in four defined spots centered about a reference spot.

The first experiment involved placement of a series of twenty microliter sample spots on SS 470 paper. Glucose reagents (Sigma 4X and SeraPak 1X) were used for the experiment. Approximately 0.5 microliters of Sigma reagent in duplicate and SeraPak reagent in duplicate were placed in the appropriate areas for simultaneous measurement. The concentrated Sigma reagent showed much faster reaction than the SeraPak reagent.

Since the test program was written to obtain simultaneous delta absorbance readings, the speed of pipetting about the circle became an important factor in determining reproducibility. The Sigma 4X spots showed delta absorbance of 159 and 208 respectively and the SeraPak spots showed delta absorbance of 112 and 109.

The experiment was a success. It was able to measure four simultaneous glucose reactions with less than 10 microliters of reagent on a diluted sample spot of 20 microliters.

The next experiment was designed to measure four separate chemistry reactions simultaneously. This required development of a five compartment grid, which consisted of four wells about a center well. The object of this grid was to permit an aligned placement of reagents on the sample spot which was keyed to the software program.

Four chemistries, triglyceride, cholesterol, uric acid and glucose were chosen. All were trinder reagents and all were measured at 500 nm. Each reagent was placed on the sample using the grid. The center well was a blank.

The experiment demonstrated that four separate chemistries can be monitored simultaneously. It also demonstrated the limitations of the manual experiments. First, the 0.5 microliter volume of reagent used was too large. It tended to diffuse into the center well, affecting the blank. Second, it was difficult to manually pipette four separate chemistries into such a precision arrangement. Third, since the program measured delta relative absorbance, it was impossible to obtain any data with precision due to the time lag from the first chemistry to the last. To be successful, an automated pipetting device must be utilized that either simultaneously drops, places, or spits the reagents onto the sample spot.

The software was refined in several ways during the course of these experiments. Initially the software did not provide adequate blanking nor was it convenient to locate the sample on the paper. In general, the intensity of illumination was non-uniform over the surface of the sample and the intensity of illumination can be expected to change during the course of the experiment.

The term "blanking" is used here to indicate the method of correcting the results for variations in illumination. To correct for spacial variations in illumination a baseline reading must be taken. This reading may be taken prior to dispensing the sample and reagents, using a perfectly white card, or it may be taken immediately following dispensing of the reagents. The latter approach appears to be preferable, in which case the results directly represent the change in reflectivity due to the reaction.

To compensate for temporal variations, all reflectivity measurements were referenced to a portion of the analytical media which was free of reactive material. That is to say the sample reflectance was represented as a fraction of the amount of light reflected from an adjacent white area. This fraction was independent of illumination intensity.

A series of experiments were then run to indicate the effectiveness of compensation for spacial and temporal variations of illumination. Simultaneous measurements were made on four widely separated areas about the test area. Ten measurements were made on each at 30 sec intervals. Without spacial compensation, the measured reflectance density varied (spot to spot) from +0.002 to −0.034. Variation with time was within +/−0.001 for each spot. When spacial compensation was used the mean spot to spot variation was +/−0.006 with an overall mean reflectance density of 0.000075. Ideally the mean reflectance density would be exactly zero. The value 0.000076 is not inconsistent with the ideal due to the nature of digitizing random noise, round-off errors in numerical calculations and the rounding of displayed results to three significant figures.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for conducting multiple chemical assays on a liquid sample in the same time and temperature dimension, comprising the following steps:

placing a volume of liquid sample about a test area on a supporting analytical media;

adding smaller separate volumes of a plurality of liquid reagents to the liquid sample at predetermined spaced-apart locations about the test area on the supporting analytical media;

causing the liquid reagents and liquid sample to mix with one another within the test area on the supporting analytical media;

simultaneously capturing at least one complete digital image of the test area;

storing each digital image of the test area; and processing each digital image of the test area to yield quantitative test results with respect to sample/reagent reactions at each spaced-apart location about the test area as a function of optical changes that have occurred at the spaced-apart locations within the test area.

2. The method of claim 1, wherein the liquid sample is directed onto an exposed absorbent surface of the supporting analytical media to impregnate the media and produce an exposed spot containing the sample.

3. The method of claim 1, wherein the liquid reagents are directed onto an exposed absorbent surface of the supporting analytical media to impregnate the media and produce a preselected pattern of exposed spots containing the reagents.

4. The method of claim 1, wherein the liquid reagents are simultaneously directed onto an exposed absorbent surface of the supporting analytical media.

5. The method of claim 1, wherein the liquid reagents are simultaneously directed onto an absorbent exposed surface of the supporting analytical media in individual volumes of one-half microliter or less.

6. The method of claim 1, wherein the step of applying the sample precedes the step of applying the reagents.

7. The method of claim 1, wherein the step of applying the reagents precedes the step of applying the sample.

8. The method of claim 1, wherein the capturing step is preceded by the following step:

drying the mixed reagents and sample within the test area on the supporting analytical media.

9. The method of claim 1, wherein the step of applying a volume of the liquid sample is carried out by placing liquid sample on the surface of an absorbent sheet.

10. The method of claim 1, wherein the step of applying a volume of the liquid sample is carried out by placing liquid sample on the surface of an absorbent sheet; and further comprising the following additional step:

drying the liquid sample on the sheet prior to the step of applying the liquid reagents.

11. An apparatus for conducting multiple chemical assays on a liquid sample in the same time and temperature dimension, comprising:

a supporting analytical media;

dispensing means for placing multiple combinations of a sample and selected reagents at predetermined spaced-apart locations about a test area on the supporting analytical media;

detection means for simultaneously capturing at least one complete digital image of the test area;

storage means for storing each digital image of the test area; and means for processing each digital image of the test area to yield quantitative test results with respect to sample/reagent reactions at each spaced-apart location about the test area as a function of optical changes that have occurred at the spaced-apart locations within the test area.

12. The apparatus of claim 11, wherein the dispensing means further includes:

multiple applicator means for simultaneously directing a plurality of liquids to the test area in predetermined spaced-apart areas.

13. The apparatus of claim 11, wherein the dispensing means further includes:

multiple reagent applicator means for simultaneously directing a plurality of reagents to the test area in predetermined space-apart locations also containing a sample.

14. The apparatus of claim 11, wherein the dispensing means further includes:

a sample applicator directing a volume of a sample within a selected test area of the supporting analytical media; and multiple reagent applicators capable of simultaneously directing a plurality of reagents onto the supporting analytical media in predetermined spaced-apart locations within the test area.

15. The apparatus of claim 11, wherein the dispensing means further includes:

a reagent applicator directing a volume of a reagent within a selected test area of the supporting analytical media; and multiple sample applicators capable of simultaneously directing a plurality of samples onto the supporting analytical media in predetermined spaced-apart locations within the test area.

16. A method for conducting multiple chemical assays on a liquid sample in the same time and temperature dimension, comprising the following steps:

placing a volume of a liquid reagent to a test area on a supporting analytical media;

adding smaller separate volumes of a plurality of liquid samples to the liquid reagent at predetermined spaced-apart locations about the test area on the supporting analytical media;

causing the liquid reagent and liquid samples to mix with one another within the test area on the supporting analytical media;

simultaneously capturing at least one complete digital image of the test area;

storing each digital image of the test area; and processing each digital image of the test area to yield quantitative test results with respect to sample/reagent reactions at each spaced-apart location about the test area as a function of optical changes that have occurred at the spaced-apart locations within the test area.

17. The method of claim 16, wherein the liquid reagent is directed onto an exposed absorbent surface of the supporting analytical media to impregnate the media and produce an exposed spot containing the liquid reagent.

18. The method of claim 16, wherein the liquid samples are directed onto an exposed absorbent surface of the supporting analytical media to impregnate the media and produce a preselected pattern of exposed spots containing the liquid reagent.

19. The method of claim 16, wherein the liquid samples are simultaneously directed onto an exposed absorbent surface of the supporting analytical media.

20. The method of claim 16, wherein the liquid samples are simultaneously directed onto an absorbent exposed surface of the supporting analytical media in individual volumes of one-half microliter or less.

21. The method of claim 16, wherein the step of applying the liquid reagent precedes the step of applying the liquid samples.

22. The method of claim 16, wherein the step of applying the liquid samples precedes the step of applying the liquid reagent.

23. The method of claim 16, wherein the capturing step is preceded by the following step:

drying the mixed reagents and sample within the test area on the supporting analytical media.

24. The method of claim 16, wherein the step of applying the liquid reagent is carried out by placing it on the surface of an absorbent sheet.

25. The method of claim 16, wherein the step of applying the liquid reagent is carried out by placing it on the surface of an absorbent sheet; and further comprising the following additional step:

drying the liquid reagent on the sheet prior to the step of applying the liquid samples.

\* \* \* \* \*